United States Patent
Holm et al.

(10) Patent No.: US 10,406,327 B2
(45) Date of Patent: Sep. 10, 2019

(54) NEEDLE TIP SHIELDING DEVICE AND FIXING ARRANGEMENT

(71) Applicant: Vigmed AB, Helsingborg (SE)

(72) Inventors: Lennart Holm, Helsingborg (SE); Robert Domonkos, Lomma (SE)

(73) Assignee: Vigmed AB, Helsingborg (SE)

( * ) Notice: Subject to any disclaimer, the term of this patent is extended or adjusted under 35 U.S.C. 154(b) by 595 days.

(21) Appl. No.: 14/397,114

(22) PCT Filed: Apr. 26, 2013

(86) PCT No.: PCT/SE2013/050471
§ 371 (c)(1),
(2) Date: Oct. 24, 2014

(87) PCT Pub. No.: WO2013/162461
PCT Pub. Date: Oct. 31, 2013

(65) Prior Publication Data
US 2015/0126931 A1    May 7, 2015

(30) Foreign Application Priority Data

Apr. 27, 2012    (SE) ........................................ 1250423

(51) Int. Cl.
*A61M 25/06*    (2006.01)
*A61M 25/00*    (2006.01)
*A61M 5/32*    (2006.01)

(52) U.S. Cl.
CPC .... *A61M 25/0618* (2013.01); *A61M 25/0014* (2013.01); *A61M 25/0606* (2013.01);
(Continued)

(58) Field of Classification Search
CPC .......... A61M 25/0618; A61M 25/0014; A61M 25/0606; A61M 2005/325; A61M 2207/00; A61M 5/3273; Y10T 29/49945
See application file for complete search history.

(56) References Cited

U.S. PATENT DOCUMENTS

| 5,135,504 A | 8/1992 | McLees |
| 6,616,630 B1 | 9/2003 | Woehr et al. |
| (Continued) | | |

FOREIGN PATENT DOCUMENTS

| DE | 202006017732 U1 | 3/2007 |
| EP | 1240916 A1 | 9/2002 |
| (Continued) | | |

OTHER PUBLICATIONS

International Search Report PCT/SE2013/050471 dated Aug. 30, 2013.
Japanese Office Action, 2015-508921, dated Jan. 13, 2017.

*Primary Examiner* — Edelmira Bosques
*Assistant Examiner* — Hamza A Darb
(74) *Attorney, Agent, or Firm* — Fishman Stewart PLLC (57) ABSTRACT

The present application discloses a needle tip shielding device for protection of a needle tip of a needle. The needle tip shielding device comprises a fixing arrangement having a proximal side and a distal side, which fixing arrangement is comprising at least one engaging element, which engaging element is resilient and resiliently striving from a compressed state towards an expanded state, in which expanded state the shortest distance between a point of said engaging element and the central axis of said needle tip shielding device is longer than the shortest distance between said central axis and any other point of said needle tip shielding device. A catheter instrument comprising the needle tip shielding device and a method for manufacturing is also disclosed.

20 Claims, 5 Drawing Sheets

(52) U.S. Cl.
CPC ..... *A61M 5/3273* (2013.01); *A61M 2005/325* (2013.01); *A61M 2207/00* (2013.01); *Y10T 29/49945* (2015.01)

(56) References Cited

U.S. PATENT DOCUMENTS

| | | | | |
|---|---|---|---|---|
| 2005/0075609 | A1* | 4/2005 | Latona | A61M 5/3273 604/164.08 |
| 2010/0204648 | A1 | 8/2010 | Stout et al. | |
| 2012/0136311 | A1* | 5/2012 | Knutsson | A61M 25/0618 604/164.08 |
| 2013/0030371 | A1* | 1/2013 | Knutsson | A61M 25/0618 604/164.08 |

FOREIGN PATENT DOCUMENTS

| | | |
|---|---|---|
| EP | 2016963 A1 | 1/2009 |
| GB | 2451153 A | 1/2009 |
| JP | 2009-545346 A | 12/2009 |
| WO | WO-2008/014908 A1 | 2/2008 |
| WO | WO-2011/019316 A1 | 2/2011 |
| WO | WO-2011129753 | 10/2011 |
| WO | WO-2012039672 A1 | 3/2012 |

\* cited by examiner

NEEDLE TIP SHIELDING DEVICE AND FIXING ARRANGEMENT

CROSS-REFERENCE TO RELATED APPLICATIONS

This application is a U.S. National phase based on PCT/SE2013/050471, filed on Apr. 26, 2013 entitled "NEEDLE TIP SHIELDING DEVICE AND FIXING ARRANGEMENT" which is based on Swedish Patent Application No. 1250423-9, filed on Apr. 27, 2012.

TECHNICAL FIELD

The present disclosure relates to a needle tip shielding device and a fixing arrangement thereof for releasable connection, in particular releasable connection to a catheter hub of a catheter instrument.

BACKGROUND

The clinical utilization of a pointed hollow needle mounted inside a flexible catheter tube is well known in the medical art for the introduction of a catheter. In such a medical instrument, the catheter tube is positioned tightly around the needle in such a way as to allow the needle to slide and telescope along the length of the catheter tube. Before use, the tip of the needle is protruding slightly through the opening of the catheter tube to allow facile penetration through the skin. Upon puncturing of the skin and introduction of the needle, the distal end of the catheter tube is simultaneously brought into place inside the desired target body cavity of the patient, such as the inside of a blood vessel, for example a vein. The needle has then done its duty in assisting the introduction of the catheter and is withdrawn by being pulled backwards through the catheter. Upon release of the needle, the catheter is set in its intended working mode extending over a lengthier period of time and including, for example, periodical administration or infusion of fluids or medications in liquid form, the collection of blood samples and the like.

An unprotected released needle constitutes, however, a serious health hazard due to the fact that it may be contaminated with e.g. infectious agents originating from the patient's blood or other body fluids, in combination with the needle tip's inherent ability to easily penetrate skin. Hence, the medical personnel who are handling the released needle may acquire the corresponding disease, e.g. HIV or hepatitis, if by accident contacting it with their skin. In order to circumvent or alleviate the health hazards associated with such a released needle amongst other things, there has been much effort devoted to the development of various kinds of needle tip protectors with a special focus on automatic variants of a type which may be referred to as being "foolproof".

Known automatic needle tip protectors of catheter instruments, utilized for introduction of a catheter tube, require means for immobilization of the needle tip protector relative the catheter hub during withdrawal of the needle from the catheter through the catheter hub. Upon disconnection of the needle tip protector from the catheter hub, in its state where it is protecting the needle tip, these means for immobilization are deactivated whereby the protector-needle tip assembly may be removed from the catheter hub-catheter assembly.

WO2011129753 describes a needle tip protector which is partially cut through with slits to allow compression of the protector when placed in the needle hub. The protector is thereby detachably held in the needle hub by a normal force in combination with inherent friction. The slits may extend essentially in the longitudinal direction of the protector, from the rear side to the front side.

Disadvantages of such means for immobilization include a relatively large variability of the force required to disconnect the protector from the catheter hub, which may adventure its intended function and safety. In this case, the large variability is due to the combination of a relative high connecting surface area between the protector and the catheter hub and the production related variability of the inner diameter of the catheter hub and the outer diameter of the protector.

U.S. Pat. No. 6,616,630 B1 discloses a safety IV catheter comprising a resilient spring clip as protector. When the needle is in the forward position, the presence of the needle forces parts of the spring clip into a position where these parts locks to the inside of the catheter hub, whereby movement of the spring clip relative the catheter hub is prevented. As the needle is withdrawn to a point where the tip passes these parts, the spring clip snaps into a position in which it is blocking access to the to the tip of the needle. Simultaneously, the part of the spring clip that previously locked to the inside of the catheter hub snap out of this position, whereby movement of the spring clip relative the catheter hub may occur.

For various reasons, including e.g. practical, economical and technical reasons, the above described spring clip, and similar marketed variants, are today by necessity made of metal and catheter hubs of a plastic material. Disadvantages of the combination of these materials in this application include the release of e.g. microscopic plastic chips and metallic particles by the scraping of the metal spring clip against the inside of the plastic catheter hub when the former is ejected from the latter upon withdrawal of the needle. These chips and particles may easily be flushed into the bloodstream of a patient upon normal use of the corresponding catheter, and thus represent a serious health hazard to the same.

GB2451153A by Poly Medicure Ltd discloses a protector capable of receiving a needle between opposing jaws attached to its base and capable of being influenced by the needle. The jaws may move between an expanded position in which they interact with an obstruction within the catheter hub. The jaws permit relative movement of the needle with the base when expanded, close around a needle tip as it passes the jaws, and release from the obstruction of the catheter hub when collapsed.

U.S. Pat. No. 5,135,504A describes a guard that may be made of a plastic material. The presence of the needle keeps the end of the guard flared out and thereby retained inside the catheter hub by e.g. a retaining ring held tightly therein until the needle is withdrawn from the catheter.

The function of the needle tip guards described in GB2451153A and U.S. Pat. No. 5,135,504A relies on the presence of one or several obstructions, e.g. protuberances or grooves, of the inside of the catheter hub for keeping the guards at place there until the needle is withdrawn from the hub. Disadvantages of the need of such obstructions include the need to use specially designed catheter hubs which are more expensive and difficult to produce in comparison to simpler standard catheter hubs.

Hence, a needle tip shielding device with improved means and structure for reversible spatial immobilization of the same relative the catheter hub, is desired.

SUMMARY

It is an object of the present disclosure, considering the disadvantages mentioned above, to provide a needle tip shielding device which may be connected in a releasable way to a standard catheter hub.

It is another object of the present disclosure, to provide a needle tip shielding device which may be produced at low cost.

It is yet another object of the present disclosure, to provide a needle tip shielding device which may be produced at low cost and connected in a releasable way to a standard catheter hub.

It is yet another object of the present disclosure, to provide a needle tip shielding device which may be connected in a releasable way to a catheter hub, with a low variation of the force needed for release across a series of individual devices. These and other objects, which will appear from the following description, have now been achieved by a needle tip shielding device for protection of a needle tip of a needle, comprising a fixing arrangement having a proximal side and a distal side, which fixing arrangement is comprising at least one engaging element, which engaging element is resilient and resiliently striving from a compressed state towards an expanded state, in which expanded state the shortest distance between a point of said engaging element and the central axis of said needle tip shielding device is longer than the shortest distance between said central axis and any other point of said needle tip shielding device.

Further features of the disclosure and its embodiments are set forth in the appended claims.

BRIEF DESCRIPTION OF THE DRAWINGS

These and other aspects, features and advantages of which the disclosure is capable will be apparent and elucidated from the following description of non-limiting embodiments of the present disclosure, reference being made to the accompanying drawings, in which.

DETAILED DESCRIPTION OF THE EMBODIMENTS

Embodiments of the present disclosure will be described in more detail below with reference to the accompanying drawings in order for those skilled in the art to be able to carry out the disclosure. The disclosure may, however, be embodied in many different forms and should not be construed as limited to the embodiments set forth herein. Rather, these embodiments are provided so that this disclosure will be thorough and complete, and will fully convey the scope of the disclosure to those skilled in the art. The embodiments do not limit the disclosure, but the disclosure is only limited by the appended patent claims. Furthermore, the terminology used in the detailed description of the particular embodiments illustrated in the accompanying drawings is not intended to be limiting of the disclosure.

Embodiments of the present disclosure will now be described below with reference to FIGS. 1 to 10. Reference to various parts of the drawings are done by numbers according to the table below.

| number | part |
| --- | --- |
| 500 | Fixing arrangement |
| 501 | Proximal side |
| 502 | Distal side |
| 511 | First stabilizing element |
| 512 | Second stabilizing element |
| 521 | First interior space |
| 522 | Second interior space |
| 531 | First outer surface |
| 532 | Second outer surface |
| 533 | Third outer surface |
| 540 | Engaging element |
| 541 | protuberance |
| 600 | Resilient arm |
| 710 | Needle |
| 711 | Needle tip |
| 712 | Restrictor |
| 713 | Connecting means |
| 810 | Catheter hub |

| number | part |
|---|---|
| 820 | Catheter |
| 1000 | Needle tip shielding device |

Figure 10:
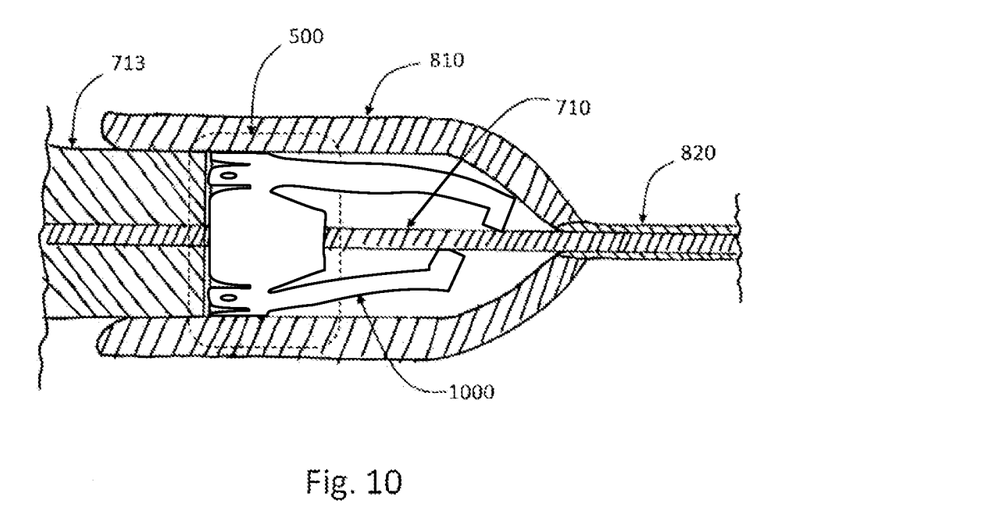
FIG. 10 is a view from the side of a catheter instrument of the disclosure in the assembled state, showing a needle tip shielding device with two resilient arms and a fixing arrangement inside a catheter hub, a needle with connecting means extending through the needle tip shielding device, the catheter hub and a catheter, according to one embodiment.

A catheter instrument of the present disclosure essentially comprises a needle 710 with a needle tip 711 at the distal end thereof, a needle tip shielding device 1000 comprising a novel and inventive fixing arrangement 500, and a catheter hub 810 having a catheter 820 extending there from.

In the ready mode, i.e. in the assembled state, and before its use for the introduction of a catheter 820, the following characteristics of the catheter instrument are valid: (i) The needle tip shielding device 1000, in its entirety or at least a part thereof, is placed in the inner space of the catheter hub 810. (ii) The needle 710 may or may not be attached to connecting means 713 at the proximal end thereof, which connecting means 713 may simultaneously and typically be dismountably attached to the proximal side of the catheter hub 810. (iii) The needle 710 is extending in a longitudinal direction, i.e. in a direction from the proximal end to the distal end of said catheter instrument, whereby it may essentially coinciding with the central axis of the needle tip shielding device 1000, the catheter hub 810 and the catheter 820. (iv) The needle tip 711 is exposed and protruding past the distal end of the catheter 820, whereby penetration of skin and placement of the distal end of the catheter 820 in a body cavity is enabled. (v) One or several resilient engaging elements 540, which may typically be rectangle or rod shaped and extending essentially parallel with the central axis and from the proximal side 501 or the distal side 502 of the fixing arrangement 500, are contacting the inner surface of the catheter hub 810, whereby the needle tip shielding device 1000 is dismountably held therein. (vi) The shaft of the needle 710 may be slidingly engaged with needle tip protective means, such as a resilient arm 600 or other such suitable means known in the art, which are thereby deactivated from protecting the needle tip 711.

When in ready mode, i.e. in the assembled state, the catheter instrument may be used by a user, such as a nurse or other medical personnel, for the introduction of the catheter 820 in accordance with the following sequential steps: (i) Penetration of the skin of a patient by means of needle tip 711, followed by insertion of the catheter 820 so that its distal opening is located in the desired body cavity, such as the inside of a vein. (ii) Fastening of the catheter hub 810 on the skin of the patient by means well known in the art, such as with medical tape or the like. (iii) Disconnection of connecting means 713, followed by withdrawal of the needle 710 by pulling the needle 710 backwards until the needle tip shielding device 1000 is disconnected from the catheter hub 810, whereby the needle tip protective means, such as a resilient arm 600 or other means known in the art, of the needle tip shielding device 1000 is protecting the needle tip 711.

After disconnection of the needle tip shielding device 1000 from the catheter hub 810, the catheter instrument is in a disassembled state. In the disassembled state, the needle tip shielding device 1000 is protecting the needle tip 711 from accidental contact. Both of the needle 710 and the needle tip shielding device 1000 are thus separated from both of the catheter hub 810 and the catheter 820. The former assembly is typically disposed of in a safe way, while the latter is typically used for administrating medicaments or taking blood samples from a patient.

According to one embodiment, the catheter instrument may be provided with connecting means 713. Connecting means 713 may be of a standard type, such as e.g. Luer-Lok®, Luer-Slip®, and various types of bayonet sockets or the like as well known in the art, for connection to the catheter hub 810. Connecting means 713 may typically comprise further means or structure for connection of the distal end of e.g. a syringe to the proximal end thereof. Connecting means 713 may be mechanically and hermetically fixed as known in the art, such as molded or glued, around the rear end of the needle 710, whereby liquid passage is allowed in both directions, from the rear end of the needle 710 to and through the needle tip 711 of the needle 710. Preferably, connecting means 713 is air tight so that no gas or liquid, such as blood or any other body liquid, may pass.

According to one embodiment, the catheter hub 810 may be provided with additional devices and the like to facilitate its placement and optimize its use, as well known in the art. For example, it may be provided with valves, gaskets, fastening devices, means for drying blood residues of the needle 710, and the like.

According to one embodiment, the needle 710 may be provided with a restrictor 712, which prevents it from being withdrawn backwards beyond a certain point, i.e. in a direction from the distal end towards the proximal end, relative the needle tip shielding device 1000. Hence, the restrictor 712 allows backward movement of the needle 710 until a needle tip protective means, such as a resilient arm 600, protects the needle tip 711. Upon further withdrawal, the needle 710 engages with the needle tip shielding device 1000, or any part thereof such as e.g. a second stabilizing element 512, by means of the restrictor 712. Even further backwards movement of the needle 710 with a slight force relative the catheter hub 810, results in transition from the assembled state to the disassembled state. The restrictor 712 may be e.g. a bump or radially expanding region of the shaft of the needle 710, or anything the like which increases the effective diameter of the shaft at a region so that it may not pass e.g. a hole that the rest of the shaft may pass. Additional examples of such a restrictor 712 include a butt weld, which may be facing away from the contact point of e.g. the resilient arm 600 on the needle 710. Examples of other possible expansion regions 305 include a crimp or any other protruding distortion as well known in the art.

Figure 8:
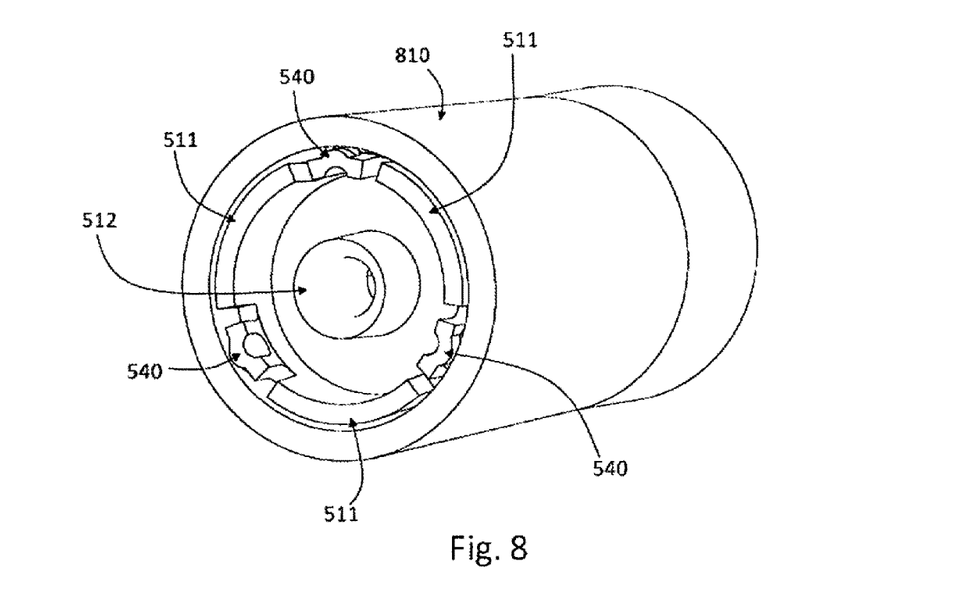
FIG. 8 is a perspective view from the rear/side of a needle tip shielding device with three engaging elements, three first stabilizing elements and one second stabilizing element comprising a circular hole, mounted in a catheter hub, according to one embodiment.
Figure 9:
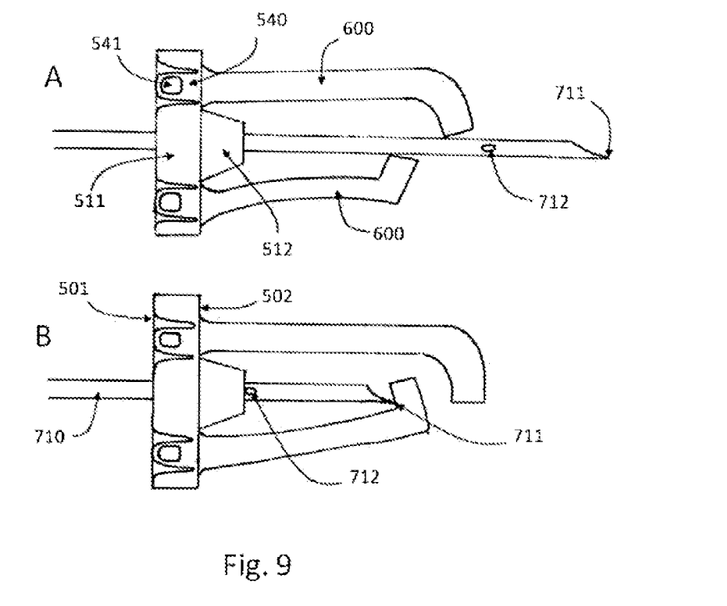
FIGS. 9A and 9B are views from the side of a needle tip shielding device according to the disclosure, showing a needle comprising a restrictor extending through a second stabilizing element with its tip past the most forwards part of two resilient arms (A), and in a backwards position wherein the restrictor is preventing further backwards movement relative the device and wherein the tip is protected from unintentional contact by the resilient arms, according to one embodiment.

A needle tip shielding device 1000 of the present disclosure essentially comprises a fixing arrangement 500 having a proximal side 501 and a distal side 502. The fixing arrangement 500 essentially comprises at least one engaging element 540, such as two or three engaging elements 540, which may be evenly spread around the outer periphery of the fixing arrangement 500 for achievement of a stable and uniform connection to the inside of the catheter hub 810. The fixing arrangement 500 may also comprise four or more, such as five, six, seven or eight, engaging elements 540, preferably evenly spread around the outer periphery of the fixing arrangement 500. Each engaging element 540 may be resilient, and thus resiliently striving from a compressed state towards an expanded state. In the expanded state, the shortest distance between an outer point of an engaging element 540 and the central axis of the needle tip shielding device 1000 is longer than the shortest distance between the central axis and any other point of the needle tip shielding device 1000. In this way, the needle tip shielding device 1000 is primarily held at place, i.e. prevented from longitudinal movement relative the catheter hub 810, by a contact point or contact surface between the inside of the catheter hub 810 and an outer point or surface of each engaging element 540.

According to one embodiment, the fixing arrangement 500 may be shaped as a circular or distorted cut cone or cylinder. A circular outer surface is particularly preferred due to the fact that most standard catheter hubs 810 have a circular interior area which the fixing arrangement 500 may be fitted to in the assembled state. The proximal side 501 and the distal side 502 may be circular and have the same diameter in the range of 3 to 6 mm, preferably 3.9 to 4.3 mm, and even more preferred 4.1 to 4.15 mm, to fit most standard catheter hubs 810.

Needle tip protective means are herein exemplified by one or several protective resilient arms 600. Other needle tip protective means are, however, well known in the art and may be applied to the needle tip shielding device 1000 of the disclosure. A resilient arm 600, with a dormant or active needle tip 711 protective function or state, may extend from the distal side of the fixing arrangement 500. The resilient arm 600 may have a relaxed state, i.e. a resting state, in which it, or any part or extension thereof, coincides with the central axis of the needle 710. In the disassembled state, the needle tip 711 may then be in direct contact with, or at least project at, the resilient arm 600, whereby it is protected by the same. The resilient arm 600 is typically striving towards its relaxed state at all times, but may be hindered to reach it by e.g. the shaft of the needle 710.

According to one embodiment, the needle tip shielding device 1000 may comprise a resilient arm 600 adapted for protecting or clamping the needle tip 711. The resilient arm 600 may extend from the distal side of the fixing arrangement 500, e.g. in the same forward direction as the longitudinal direction of the needle 710 in the assembled state. The resilient arm 600 may have a resting state, from which it may be forced to yield free passage in an axial direction of the fixing arrangement 500. The shaft of the needle 710 may e.g. contact the resilient arm 600 to yield such free passage, whereby the needle 710 may be moved back and forth in a longitudinal direction relative the needle tip shielding device 1000. In the resting state, or in a state between the resting state and the state in which it has been forced out from the resting state by e.g the shaft of the needle 710, any straight imaginary line extending longitudinally in the axial direction of the fixing arrangement 500 through a passage between the proximal side 501 and the distal side 502 may coincide with the resilient arm 600.

According to one embodiment, the needle tip shielding device 1000 may comprise a resilient arm 600, adapted for protecting or clamping the needle tip 711, and the needle 710 may be provided with a restrictor 712, for prevention of backwards movement relative the needle tip shielding device 1000 beyond a certain point. When the needle 710 has been withdrawn to the point where restrictor 712 reaches the contact point of the resilient arm 600, the latter may bend away slightly to allow easy passage of the former upon a slight increase in the force of withdrawal. If the restrictor 712 is of a particular type and located on the needle 710 such that the resilient arm does not come in contact with any area with increased effective diameter, the resilient arm does not have to bend away slightly. Further withdrawal of the needle 710, to the point where the needle tip 711 passes the contact point of the resilient arm 600, results in that the former is no longer in a forward position and that the latter strives toward its normal resting position, which is such that a part of the resilient arm 600, or an extension thereof, is in front of the needle tip 711. The resting position of the resilient arm 600 is such that the needle tip 711 may, preferably, always project, in the longitudinal direction of the needle 710, onto a point of the surface of the resilient arm 600 independent of the degree of rotation of the needle 710 around its longitudinal axis. The needle tip 103 is thus clamped and protected by the resilient arm 600. When drawn backwards beyond this point, the needle 710 may not be pushed in the forward direction again without being hindered by the resilient arm 600, or an extension thereof. Hence, if a user tries to push the needle 710 forwards, the needle tip 711 may penetrate slightly into a plastic or polymeric resilient arm 600. Even further withdrawal of the needle 710, to the point where the restrictor 712 reaches the fixing arrangement 500, or any part thereof such as a second stabilizing element 512 comprising a longitudinally extending hole adapted for encompassing the shaft of the needle 710, results in that the needle 710 engages with, i.e. gets stuck in, the needle tip shielding device 1000, such as e.g. in the hole of the second stabilizing element 512. Additional increase in the force of withdrawal of the needle 710 results in that the needle tip shielding device 1000 disconnects from the catheter hub 810, i.e. in transition from the assembled state to the disassembled state. The needle 710 is thereby released from the catheter hub 810 together with the needle tip shielding device 1000, which is effectively clamping the needle tip 711 and protecting a user from accidental contact with the same. The force needed to disconnect the needle tip shielding device 1000 from the catheter hub 810 is mainly dependant on the design of the fixing arrangement 500. For example, an increase in the number of engaging elements 540 thereof, increases this force. An increase in the resilient force towards an expanded state of these, or an increase of the friction of the contacting area or point against the inside of the catheter hub 810, also increases this force. The one skilled in the art is well aware of how the fixing arrangement 500 may be designed by alteration of properties of its engaging elements 540 to achieve a desired force of transition from the assembled state to the disassembled state. Preferably this force is such that the needle tip shielding device 1000 is not disconnected from the catheter hub 810 when the needle 710 is withdrawn until the restrictor 712 reaches the fixing arrangement 500. The needle tip shielding device 1000 is, however, preferably easily disconnected when the restrictor 712 reaches the fixing arrangement 500, such as with, for example, a gentle jerk backwards. When the needle 710 and the needle tip shielding device 1000 have been released from the catheter hub 810, or when the needle tip shielding device 1000 is fitted inside the catheter hub 810 and the needle tip 711 is clamped by the resilient arm 600, or an extension thereof, the needle 710 might be pushed forward so that the rear end of the restrictor 712 is moved forward a distance of 0 to 2 mm, such as 0 to 0.5 mm, from the most forward edge of the fixing arrangement 500, during which the needle tip 711 may slide on the surface of the resilient arm 600 until it coincides with e.g. a corner thereof or penetrates slightly therein.

According to one embodiment, the needle tip shielding device 1000 may comprise one, two, three or more engaging elements 540, and at least one thereto adjacent first interior space 521. The engaging elements 540 may be resilient, whereby they are resiliently striving from a compressed state towards an expanded state. In the assembled state, the engaging elements reside in a state between the compressed and the expanded state, whereby they are contacting the inner surface of the catheter hub 810 with a force. The needle tip shielding device 1000 is thereby held therein, i.e. a constant spatial relationship between the needle tip shielding device 1000 and the catheter hub 810 is provided. Any first interior space 521 may be located between the central axis of the needle tip shielding device 1000 and the engaging element 540. A part of the outer surface of any first interior space 521 is essentially adjacent to the corresponding engaging element 540. Relative movement of the engaging element 540 from the expanded state to the compressed state is thereby enabled. A plurality of engaging elements 540 may be evenly spread at the periphery of the fixing arrangement 500, whereby each engaging element 540 is contacting the inner surface of the catheter hub 810 with essentially the same force. Each engaging element 540 is adapted such that it may be moved in a direction perpendicular to the axial extension of the needle tip shielding device 1000, from the compressed to the expanded state or vice versa, unless hindered by the inner surface of the catheter hub 810 to fully reach the expanded state. An adjacent first interior space 521 enables the engaging element 540 to attain a compressed state without any mechanical hindrance by any part of the needle tip shielding device 1000. The needle tip shielding device 1000 may thus be mounted in the catheter hub 810 when all its engaging elements 540 are in the compressed state, or a state near the compressed state, followed by expansion towards the expanded state therein to contact the inner surface of the catheter hub 810 with a force. A plurality of engaging elements 540 may have a common first interior space 521 or separate interior spaces 521.

Figure 1:
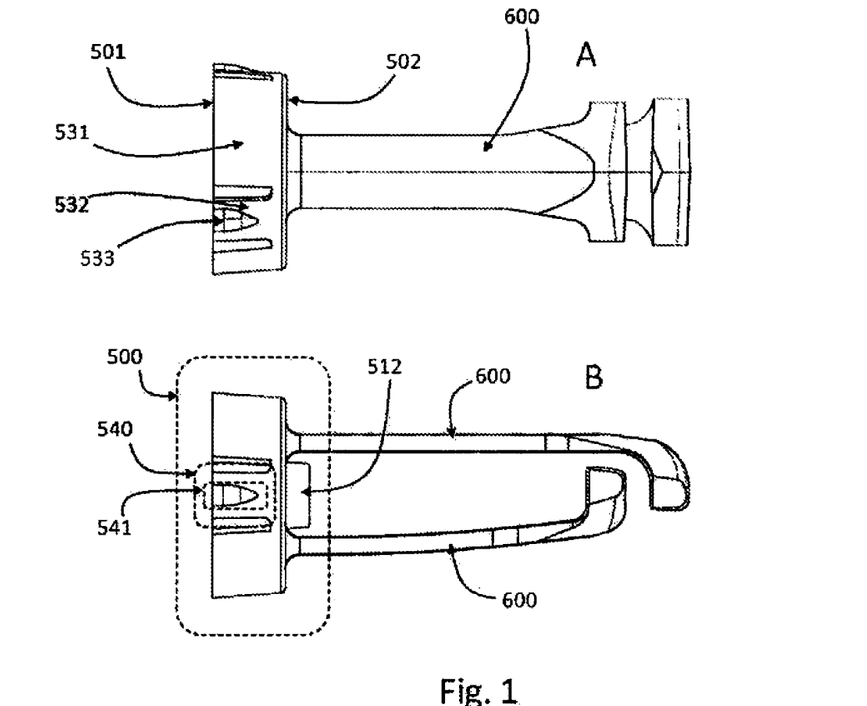
FIGS. 1A and 1B are views from the side of a needle tip shielding device according to the disclosure, with fixing arrangement comprising backwards extending engaging elements, each with a protuberance for contacting the inside of a catheter hub, and with backwards extending first stabilizing elements and forwards extending resilient arms, according to one embodiment.
Figure 2:
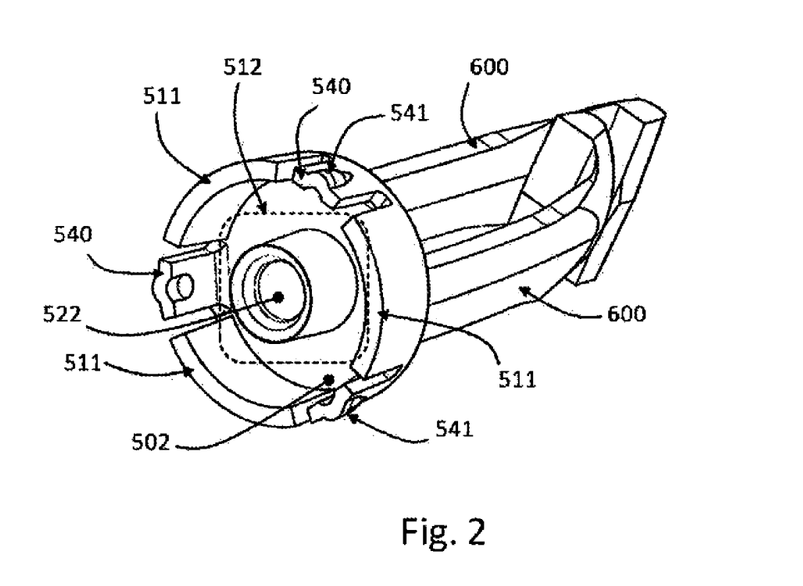
FIG. 2 is a perspective view from the rear side of the needle tip shielding device of FIG. 1, showing a fixing arrangement with a hollow interior and a centrally positioned second stabilizing element with a slanting surface leading to a central hole, for the shaft of a needle to pass through, according to one embodiment.
Figure 3:
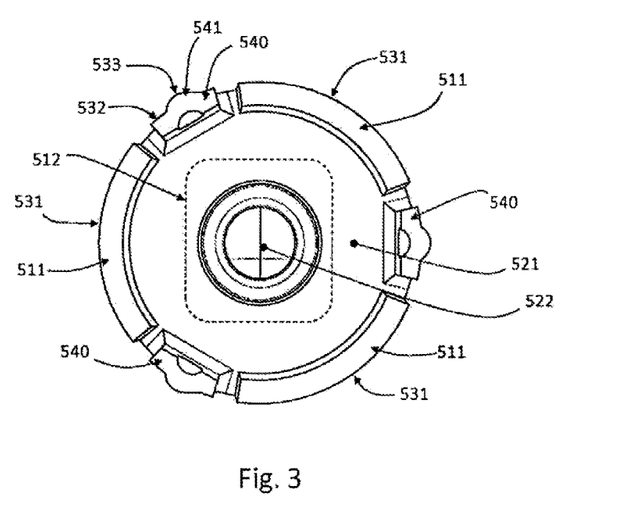
FIG. 3 is a view from the rear side of the needle tip shielding device of FIGS. 1 and 2, according to one embodiment.
Figure 4:
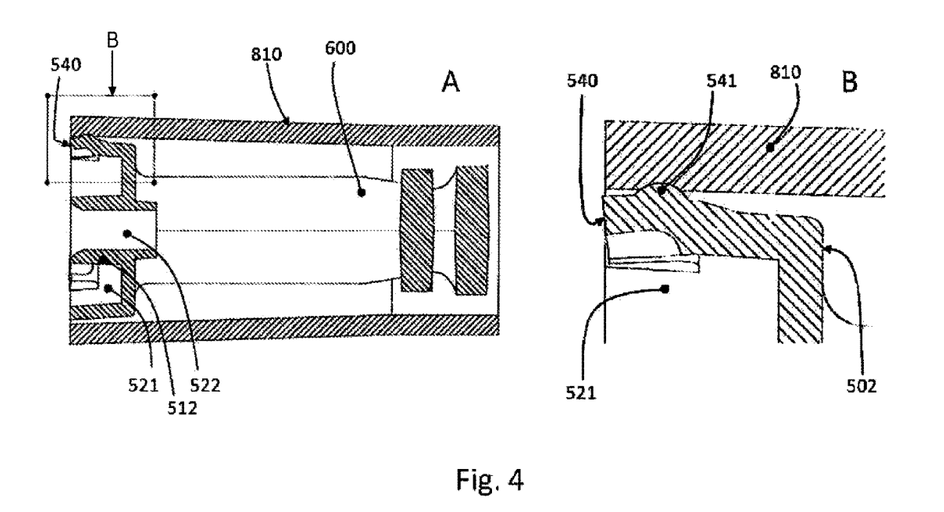
FIGS. 4A and 4B are a full view from the side (A) and a blown up view from the side (B) of a needle tip shielding device with an engaging element with a protuberance with slanting proximal and distal surfaces mounted in a catheter hub, the protuberance is making an imprint in the catheter hub, according to one embodiment.
Figure 5:
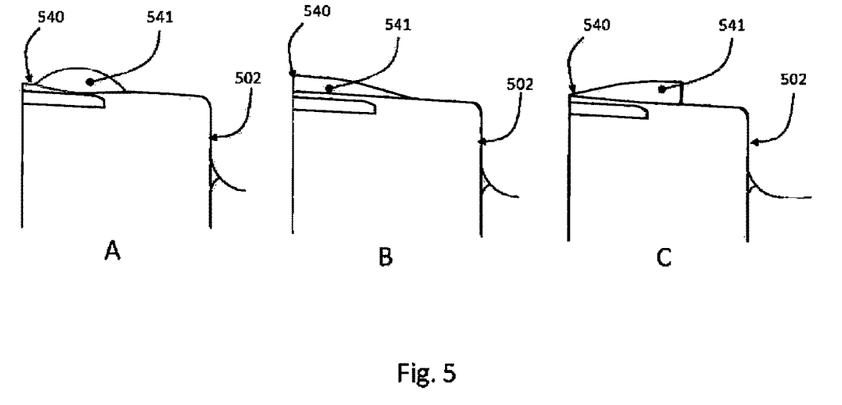
FIGS. 5A, 5B and 5C are blown up views from the side of a needle tip shielding device with an engaging element with a protuberance with slanting surfaces at its proximal end and at its distal end (A), at its distal end only (B) and at its proximal end only (C), according to one embodiment.
Figure 6:
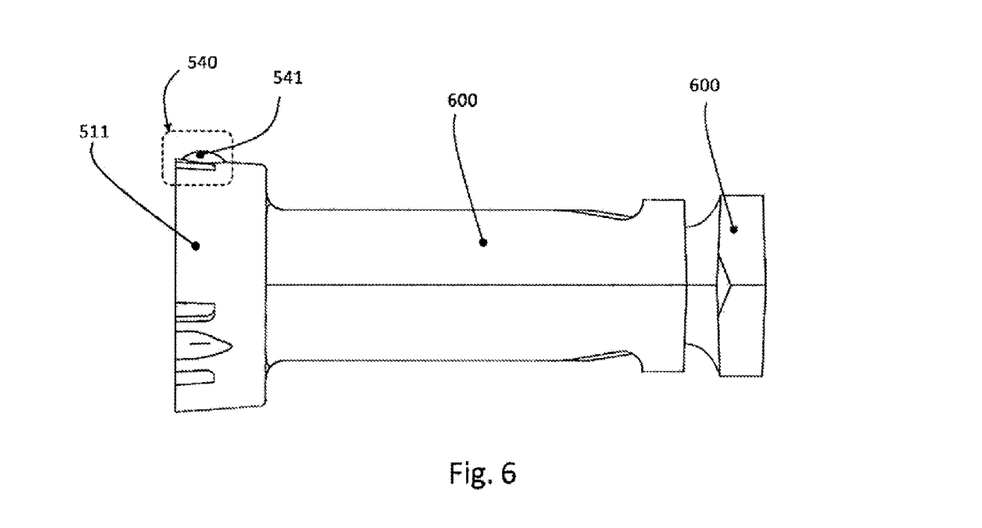
FIG. 6 is the full view of the needle tip shielding device of FIG. 5A, according to one embodiment.
Figure 7:
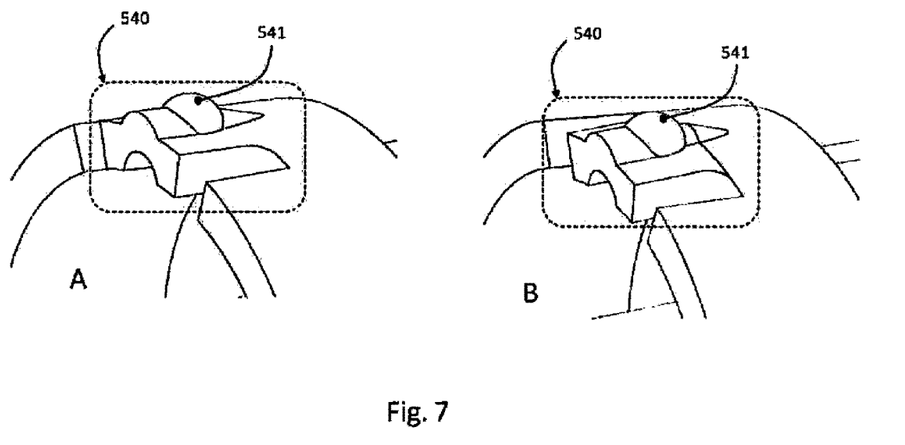
FIGS. 7A and 7B are perspective views from the rear/side of a part of a needle tip shielding device showing an engaging element in the expanded state (A) and in the compressed state (B), according to one embodiment.

According to one embodiment, the fixing arrangement 500 of the needle tip shielding device 1000 may be hollow. Hence, engaging elements 540 may have a common first interior space 521 as represented by this hollow part. Advantages of such a hollow fixing arrangement 500 include a reduced production cost due to the need of less material in comparison to a needle tip shielding device 1000 with a denser fixing arrangement 500. When provided with one or several first stabilizing elements 511 and a second stabilizing element 512, the fixing arrangement 500 may be provided with one or several reinforcement elements, as well known in the art, which connect the former with the latter. Such reinforcement elements will provide the first stabilizing element 511 with additional resistance against forces from e.g. the catheter hub 810. The first stabilizing element 511 may thus not have to be as thick as the case without such reinforcement elements.

According to one embodiment, one or several, preferably all if any, of the engaging elements 540, may comprise a protuberance 541 extending in a direction essentially perpendicular to the central axis of the needle tip shielding device 1000. In the assembled state, a third outer surface 533 of this protuberance 541 is contacting the inner surface of the catheter hub 810. The third outer surface 533 may be provided with means for increasing the friction against the catheter hub 810, whereby the needle tip shielding device 1000 is more securely held therein. Examples of such means include grooves or any other suitable deviation from a smooth surface. Hence the outer surface 533 may be e.g. etched or blasted.

According to one embodiment, the protuberance 541 may be circular or elliptic. The contact point or surface with the catheter hub 810 is preferably located at or near the center of such a circular or elliptic protuberance. The protuberance 541 may have at least one sloping end for enabling the needle tip shielding device 1000 to be smoothly mounted in, and/or withdrawn from, the catheter hub 810. For example, the end which is facing in the same direction as the proximal side 501, may be sloped for enabling smooth withdrawal. The end, which is facing in the same direction as the distal side 502, may be sloped for enabling smooth mounting of the needle tip shielding device 1000 from the proximal side of the catheter hub 810.

According to one embodiment, the fixing arrangement 500 may comprise at least one, such as e.g. two or preferably three, first stabilizing elements 511. Such first stabilizing elements 511 may typically be shaped as bent sheets, with a thickness of 0.5 to 2 mm, such as about 0.8 mm, having a first outer surface 531 and curvature adapted to fit against the adjacent inner surface of the catheter hub 810 in the assembled state. They may be thicker than the corresponding engaging elements 540, as they may preferably not bend away as easily from an externally applied force. Their longitudinal extension may be essentially parallel with the central axis. They may extend from the proximal side 501 or the distal side 502 of the fixing arrangement 500. Advantages of such first stabilizing elements 511 include minimization of the risk for the needle tip shielding device 1000 to wobble in the catheter hub 810, i.e. minimization of the risk of movement resulting in that the central axis of the needle tip shielding device 1000 is not coinciding with the central axis of the catheter hub 810. Additional advantages include a minimization of the risk of erroneous mounting the needle tip shielding device 1000 in the catheter hub 810 in such a way that the central axis of the needle tip shielding device 1000 is not coinciding with the central axis of the catheter hub 810. Such wobbling or erroneous mounting may adventure the intended function of the engaging elements 540. Hence, first stabilizing elements 511 stabilize the needle tip shielding device 1000 in the catheter hub 810 by interacting with the inner surface of the catheter hub 810, whereby the central axis of the needle tip shielding device 1000 is kept in an essentially coinciding relationship with the central axis of a catheter hub 810, in particular a tubular catheter hub 810.

According to one embodiment, the needle tip shielding device 1000 comprises a second stabilizing element 512. The second stabilizing element 512 may be located at the center of the fixing arrangement 500 and provided with a passage from the proximal side 501 to the distal side 502. It stabilizes the longitudinal movement of the needle 710, i.e. in a direction along the central axis of the needle tip shielding device 1000 and relative the same. The central axis of the needle 710 is thus always essentially parallel with the central axis of the needle tip shielding device 1000. The passage from the proximal side 501 to the distal side 502 has a second interior space 522, encompassed by the inner surface of the second stabilizing element 512, through which the needle 710 extends and may be moved in a longitudinal direction. The needle 710 is thus slidingly engaged with the inner surface of the second stabilizing element 512. The inner surface may comprise one or several contact surfaces or one or several contact points, which are contacting the shaft of the needle 710. A suitable second interior space 522 may be a circular hole with a diameter equal to or slightly larger than the outer diameter of the shaft of the needle 710. Preferably the contact area of the hole is arranged such that a maximal contact with needle shaft is achieved without preventing the sliding of the needle 710 through the needle tip shielding device 1000. The extension of such a hole in the longitudinal direction may be such that it sufficiently stabilizes longitudinal movement of the needle 710 relative the needle tip shielding device 1000. A suitable combination of the extension of such a hole in the longitudinal direction and its diameter is well known to the skilled person.

According to one embodiment, the proximal side of the second stabilizing element 501 may be provided with a recess. Then the mouth of the passage, e.g. a hole, is provided at the bottom of the recess. The recess then preferably has slanting surfaces, such as forming a cone-shaped recess. The recess of this kind on the proximal side of the second stabilizing element 512 may guide the needle 710 through the passage during mounting of the needle tip shielding device 1000 on the needle 710.

According to one embodiment, the distal side of the second stabilizing element 501 may be provided with a recess. Then the mouth of the passage, e.g. a hole, is provided at the bottom of the recess. The recess then preferably has slanting surfaces, such as forming a cone-shaped recess. The recess of this kind on the distal side of the second stabilizing element 512 may guide the needle 710 through the passage during mounting of the needle tip shielding device 1000 on the needle 710.

According to one embodiment, the distal side 502 may be provided with a cone-shaped elevation, which constitutes a part of the second stabilizing element 512, through which the passage from the proximal side 501 to the distal side 502, e.g. a hole, is extending. The effective length of the passage is thereby increased which, for example, allows a better guidance of the needle 710 without having to increase the area of the outer surface of the fixing arrangement 500, which is adjacent to the inner surface of the catheter hub 810. Furthermore, the cone-shaped area might be provided with means known in the art, such as a circular scraper, which cleans off residues of e.g. blood from the needle 710 as this is withdrawn.

According to one embodiment, the needle tip shielding device 1000 may comprise at least one, such as e.g three, first stabilizing elements 511, at least one, such as e.g. three, engaging elements 540, and one second stabilizing element 512. The latter may comprise a longitudinal hole through which the needle 710 may extend. The combination of three first stabilizing elements 511 and three engaging elements 540, which all are consecutively and evenly spread, provide a particularly advantageous needle tip shielding device 1000 due to their direct or indirect interaction with each other in the assembled state. This combination is furthermore a preferred combination which demands the fewest of each of first stabilizing elements 511 and engaging elements 540.

The various parts of the fixing arrangement 500, their function and interaction with each other and other parts of the catheter instrument, are described herein above and illustrated in the appended Figures. Herein below follows an alternative description of the fixing arrangement 500 in order for the skilled person to understand how the used terminology may be interpreted for the practical realization of the disclosure.

According to one embodiment, the fixing arrangement 500 may comprise a circular disc with a front side corresponding to the distal side 502, and with a back side facing in the same direction as the proximal side 501. The circular disc may comprise a central cylinder or cone shaped object, which corresponds to the second stabilizing element 512, extending in a longitudinal direction, i.e. in a direction perpendicular to the plane of the circular disc. The central cylinder or cone shaped object has a distal end, which may be located at or in front of the front side of the circular disc, and a proximal end, which may be located at or proximal to the back side of the circular disc. The central cylinder or cone shaped object may comprise a central circular hole or other suitable space with a central axis, extending in a longitudinal direction from the distal end to the proximal end thereof, to allow the back and forth movement along this central axis of a needle 710 by slidingly supporting its shaft.

At least one, such as both, of the proximal end and the distal end of the central cylinder or cone shaped object is preferably extending beyond the back side and the front side, respectively, of the circular disc. The supporting area of the central circular hole is thus increased and the support of the sliding needle 710 is improved in comparison to the case of e.g. a hole at the center of the circular disc. Resilient flaps, corresponding to engaging elements 540, may extend backwards in a longitudinal direction from the back side of the circular disc at or near the periphery of the same, i.e. at a point at or near the circumference of the circular disc. The outer surface of the flaps, i.e. the surface which is facing away from the central axis and radially outwards from the circular DISC, may essentially coincide with the circular area defined by the longitudinal projection of the circumference of the circular disc. The longitudinal projection of the circumference of the circular disc may be in the form of a flange, that extends parallel to the central axis of the central circular hole. The resilient flaps and the flange from which the resilient flaps are cut out, may extend distally or proximally. When the resilient flaps and the flange extend proximally, insertion of the needle tip shielding device 1000 into the catheter hub 810 may be facilitated, and when the resilient flaps and the flange extend distally, withdrawal of the needle tip shielding device 1000 from the catheter hub 810 may be facilitated. Each of these flaps may be provided with an extension, corresponding to protuberance 541, located at the outer surface thereof. This extension extends radially outwards from the flange. Thus, this extension may extend beyond this circular area in a direction perpendicular to the central axis. The resilient flaps may be forced towards a compressed state, e.g. by the inside of a catheter hub 810, such that the outermost point of an extension at the outer surface thereof substantially coincides with the circular area defined by the longitudinal projection of the circumference of the circular disc. In this way a stabilized fit between the needle tip shielding device 1000 and the catheter hub may be obtained, since the resilient flaps, with radial extensions, may compensate for unevenness on the inside of the catheter hub 810, and further allowing more than three extensions while still maintaining stabilized fit within the catheter hub with simultaneous increased retaining force. The flange, in accordance with above, may be described as essentially rigid mechanically supporting elements, corresponding to first stabilizing elements 511, extending backwards—or forward, in accordance with above—in a longitudinal direction from the back side of the circular disc at or near the periphery of the same, i.e. at a point at or near the circumference of the circular disc. The outer surface of these elements, i.e. the surface which is facing away from the central axis, may essentially coincide with the circular area defined by the longitudinal projection of the circumference of the circular disc. The supporting elements and the resilient flaps may thus be equally spatially arranged in relationship to the circular disc. They are preferably arranged symmetrically in relationship to each other, with a separating distance of e.g. 0.1 to 3 mm between each other to enable proper function. Such a symmetric relationship results in optimal stability and control of the withdrawing force needed to remove the needle tip shielding device 1000, comprising a fixing arrangement 500, from e.g. a catheter hub 810, in comparison to any other corresponding asymmetric relationship.

According to one embodiment, the needle tip shielding device 1000 may be made of a plastic material. Preferably, the plastic material has a suitable combination, for its intended purpose, of tenacity, rigidity, fatigue resistance, elasticity, and creep deformation resistance. The selection of a suitable plastic material may easily be made by the one skilled in the art. The one skilled in the art may also perform standard experiments in order to screen a range of plastic materials, whereby a suitable plastic material may be selected on the basis of the results of such experiments. A suitable plastic material has a high creep deformation resistance, i.e. it has a low tendency to slowly move or deform permanently under the influence of an applied external pressure. Hence, a catheter instrument of the present disclosure, comprising for example engaging elements 540 with protuberances 541, may be stored in the assembled ready mode for a prolonged time without extensive creep deformation of protuberance 541, which would otherwise make the needle tip shielding device 1000 more prone to involuntary disconnection from the catheter hub 810. A suitable plastic material has, furthermore, a suitable elasticity and high three-dimensional memory to allow for an engaging element 540 to retain its expanded state and hold the needle tip shielding device 1000 in the catheter hub 810 even after prolonged storage, during which the engaging element 540 has been forced out of this state. In addition, the tenacity of the plastic material is preferably such that the needle tip 711 may penetrate slightly into, but not through the same. Advantages of a plastic needle tip shielding device 1000 include the highly reduced tendency, in comparison to metal, of release of e.g. microscopic plastic chips by the scraping of the plastic catheter hub 810 when the needle tip shielding device 1000, or a corresponding device, is ejected from the former upon withdrawal of the needle 710. Accordingly, the tendency for formation of scrape marks, which may result in leakage through the affected connector, is greatly reduced. In addition, a plastic needle tip shielding device may be easily color coded or transparent, depending on its particular application.

According to one embodiment, the needle tip shielding device 1000 may be a monolithic or homogenous injection molded needle tip shielding device 1000 made of a molded plastic material. Due to the specific configuration of the different parts of the needle tip shielding device 1000 according to the embodiments of the present disclosure, the needle tip shielding device 1000 may be molded, such as injection molded, into one homogenous, i.e. monolithic, piece and/or one integral unit, without interfaces in between the different parts thereof. Advantages of a monolithic needle tip shielding device 1000 include a lower production cost in comparison to other devices made of more than one part that has to be assembled.

According to one embodiment, the needle tip shielding device 1000 may be made of a thermoplastic polymer comprising crystalline and amorphous alternating regions. When the needle tip shielding device 1000 is made of a thermoplastic polymer comprising crystalline and amorphous alternating regions, the needle tip shielding device 1000 will have enhanced storing capacity, due to the excellent structure memory of these polymers. The amorphous regions contribute elasticity and the crystalline regions contribute strength and rigidity, which will render the needle tip shielding device 1000 excellent for being stored in a strained state with minimal lost of resiliency.

According to one embodiment, the needle tip shielding device 1000 may be made of a plastic material selected from the group comprising of POM, PBTP, PMMA, ABS, SAN, ASA, PS, SB, LCP, PA, PSU, PEI, PC, PPO, and/or PPO/SB. These polymers have specifically the advantages according to above, without necessarily being thermoplastic polymers with crystalline and amorphous alternating regions.

According to one embodiment, the needle tip shielding device 1000 may be made of a thermoplastic elastomer selected from the group comprising of a styrenic block copolymer, a polyolefinic mixture, an elastomeric alloy, a thermoplastic polyurethane, a thermoplastic copolyester, and/or a thermoplastic polyamide. Also these polymers have specifically the advantages according to above.

According to one embodiment, the needle tip shielding device 1000 may be made of a plastic material selected from the group comprising of Styroflex®, Kraton®, Pellethane®, Pebax®, Arnitel®, Hytrel®, Dryflex®, Santoprene®, Geolast®, Sarlink®, Forprene®, Alcryn®, and/or Evoprene®, for the same reasons as above.

According to one embodiment, the needle tip shielding device 1000 may be made of a plastic material selected from the group comprising of medical grade liquid crystal polymer, for example Vectra® LCP, polyethylene, and/or ultra high molecular weight polyethylene, for the same reasons as above.

According to one embodiment, the needle tip shielding device 1000 may be made of polysulfon, polyoxymetylen or polycarbonate.

Contacting smooth shapes of two bodies, such as a needle tip shielding device mounted in a catheter hub, may result in a significant attraction between these bodies, especially if the contact area is large and they are pressed together. The underlying basis for this type of attraction include intermolecular attraction between the molecules of the two bodies, in which molecular van der Waals interactions and surface tension of the two bodies are important factors. Covalent bond formation between closely interacting surfaces may also contribute to the attraction. Such covalent bond formation, and other types of attraction between two surfaces, may also result upon radiation treatment, such as radiation treatment of e.g. catheter instrument to sterilize these. This type of attraction may become noticeable when the needle tip shielding device, or a part thereof, is about to be released from e.g. a catheter hub. The force needed to release the needle tip shielding device, or a part thereof, from the hub then becomes significantly higher than expected. This effect, which may be referred to as "the attraction effect", may even adventure the intended function of the needle tip shielding device if relying on e.g. an automatic release of a part of the device, such as a spring biased arm or the like, from a part of the catheter hub.

According to one embodiment, the contacting part or the whole of the needle tip shielding device 1000 and the catheter hub 810 of the catheter instrument may be made of two different polymeric or plastic materials. The needle tip shielding device 1000 is kept in contact with the catheter hub 810 in the assembled state via at least one interface surface between the needle tip shielding device 1000 and the catheter hub 810. If this interface surface is constituted, fully or partly, of two different materials, disadvantages related to the attraction effect are minimized. For example, the plastic or polymeric material of the needle tip shielding device 1000 may be polyoxymethylene (POM), polybutylen terephthalate (PBTP) or polysulfone (PSU), or any other material as known in the art with similar suitable properties. The plastic or polymeric material of the needle tip shielding device 1000 may accordingly be different from the material of the catheter hub 810 in order to minimize the attraction effect. A majority of standard catheter hubs 810 are made of at least one polymer produced from substituted or unsubstituted ethene by a polymerization reaction in which the double bond of said ethane is converted to a single bond, for example polypropylene, polyethylene, or propylene/ethylene co-polymers. Thus, POM, PBTP, PSU or polycarbonate, or any other material as known in the art with similar suitable properties which is not the same as the material of the catheter hub 810, may advantageously be used as the material of a generally applicable needle tip shielding device 1000.

According to one embodiment, the interface surface between the needle tip shielding device 1000 and the catheter hub 810 may be provided with an anti-adhesive agent. If the interface surface is constituted by the same type of plastic or polymeric material of the needle tip shielding device 1000 and the catheter hub 810, disadvantages related to the attraction effect may be minimized by employment of such an anti-adhesive agent. Basically, a suitable anti-adhesive agent is a fine-grained solid, semi-solid, amorphous material or liquid which is made of one or several materials which are all different from both of the contacting surfaces of the needle tip shielding device 1000 and the catheter hub 810. It is preferably a non-lubricant, or has only weak lubricating properties, to minimize the risk of undesired disconnection of the needle tip shielding device 1000 from the catheter hub 810. It is preferably of a medically accepted type and grade with low toxicity. Examples of suitable anti-adhesive agents include polysaccharides, non-toxic salts such as magnesium or calcium carbonate, or the like. Additional examples include any suitable pharmaceutically acceptable carrier or excipient, which may easily be selected by the skilled person for this application.

According to one embodiment, the catheter instrument may be manufactured by mounting the needle tip shielding device 1000 in the catheter hub 810, e.g. by pressing the needle tip shielding device 1000 into the catheter hub 810 in a direction from the proximal end towards the distal end of the catheter hub 810. The needle 710 may already be mounted in the needle tip shielding device 1000, when the latter is mounted in the catheter hub 810.

According to one embodiment, the needle 710 may be mounted in the catheter hub 810 by the following consecutive steps: a) Introduction of the needle 710, with the needle tip 711 first, in a direction from the proximal side 501 towards the distal side 502 through the second stabilizing element 512; b) Provision of restrictor 712 on the shaft of the needle 710 by e.g. pressing the shaft slightly or providing a butt weld thereon. This order of steps is advantageously used for needle tip shielding devices 1000, such as needle tip shielding devices 1000 described in embodiments herein, wherein the shaft of the needle 710 may be reached for the provision of restrictor 712, when the former is mounted in the latter.

According to one embodiment, the needle 710 may be mounted in the catheter hub 810 by the following consecutive steps: a) Provision of restrictor 712 on the shaft of the needle 710 by e.g. pressing the shaft slightly or providing a butt weld thereon; b) Introduction of the needle 710, with the rear side of the needle 710 first, in a direction from the distal side 502 towards the proximal side 501 through the second stabilizing element 512. Step b) may optionally be followed by mounting connecting means 713 at the rear end of the needle 710. This order of steps is advantageously used for needle tip shielding devices 1000 wherein the shaft of the needle 710 may not be reached for the provision of restrictor 712, when the former is mounted in the latter.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc. do not preclude a plurality. Reference signs in the claims are provided merely as a clarifying example and shall not be construed as limiting the scope of the claims in any way.

The invention claimed is:

1. A catheter instrument comprising a needle having a needle tip at a distal end thereof, a needle tip shielding device, and a catheter hub having a catheter extending from the distal end thereof, wherein:

said catheter instrument has an assembled state, said needle extending in a direction from a proximal end to a distal end of said catheter instrument substantially coinciding with a central axis of said needle tip shielding device, said catheter hub, and said catheter, and in which said assembled state said needle tip is exposed and protruding past the distal end of said catheter, for enabling penetration of a skin and placement of said distal end of said catheter in a body cavity;

said catheter instrument has a disassembled state, said needle tip shielding device is protecting said needle tip from accidental contact, both of said needle and said needle tip shielding device is separated from both of said catheter hub and said catheter;

said needle tip shielding device comprising a fixing arrangement with a proximal side and a distal side, the fixing arrangement comprising a plurality of engaging elements with sidewalls forming gaps, interposed by stabilizing elements, and in a substantially concentric arrangement with the stabilizing elements, said plurality of engaging elements extending substantially parallel with said central axis from said proximal side or said distal side, said plurality of engaging elements is resilient and expandable in a radially outward direction from a compressed state towards an expanded state, such that said plurality of engaging elements is contacting an inner surface of said catheter hub with a force in said assembled state for providing a constant spatial relationship between said needle tip shielding device and said catheter hub in said assembled state; and said needle tip shielding device is comprising at least one resilient arm extending from the distal side of said plurality of engaging elements, the resilient arm, or a part thereof, coincides with the central axis of said needle in said disassembled state.

2. The catheter instrument according to claim 1, wherein the stabilizing elements include a first stabilizing element and a second stabilizing element, and said fixing arrangement comprises said first stabilizing element, a first interior space, and said second stabilizing element;

said first stabilizing element comprises a first outer surface said first outer surface having substantially a same shape as an adjacent part of the inner surface of said catheter hub in said assembled state for stabilizing said needle tip shielding device in said catheter hub;

said first interior space is located between the central axis of said needle tip shielding device and said plurality of engaging elements and adjacent to said plurality of engaging elements for enabling relative movement of said plurality of engaging elements from said expanded state to said compressed state; and said second stabilizing element comprises a second interior space which second interior space is encompassing a shaft of said needle said second stabilizing element having at least one of i) one or several contact points, ii) one or several contact surfaces, or iii) a mixture of at least one contact point and at least one contact surface, which points or surfaces are slidingly engaged with the shaft of said needle, for stabilizing movement of said needle in a direction along the central axis of said needle tip shielding device and relative said needle tip shielding device.

3. The catheter instrument according to claim 1, wherein said plurality of engaging elements comprises a protuberance, said protuberance is extending in a direction substantially perpendicular to the central axis of said needle tip shielding device, and said protuberance comprises a third outer surface or contact point at a distal end which is contacting the inner surface of said catheter hub with a second force in said assembled state, for providing a releasable connection between said plurality of engaging elements and said catheter hub.

4. The catheter instrument according to claim 1, wherein the stabilizing elements include a second stabilizing element, and said needle comprises a restrictor for engagement with said second stabilizing element upon maximal movement of said needle relative said needle tip shielding device in a direction from the distal end towards the proximal end of said needle tip shielding device.

5. The catheter instrument according to claim 1, further comprising connecting means at the proximal end of said needle for connection to said catheter hub.

6. The catheter instrument according to claim 1, wherein said needle tip shielding device is kept in contact with said catheter hub in said assembled state via at least one interface surface between said needle tip shielding device and said catheter hub, said at least one interface surface of said needle tip shielding device being fully or partly made of a first polymeric material and said at least one interface surface of said catheter hub being fully or partly made of a second polymeric material.

7. The catheter instrument according to claim 1, wherein said needle tip shielding device is kept in contact with said catheter hub in said assembled state via at least one interface surface between said needle tip shielding device and said catheter hub, said at least one interface surface comprising an anti-adhesive agent between said at least one interface surface of said needle tip shielding device and said at least one interface surface of said catheter hub.

8. A method for the manufacture of a catheter instrument according to claim 1, comprising the step of mounting said needle tip shielding device in said catheter hub by pressing said needle tip shielding device into said catheter hub in a direction from the proximal end towards the distal end of said catheter hub.

9. A needle tip shielding device for protection of a needle tip of a needle, comprising a fixing arrangement having a proximal side and a distal side, the fixing arrangement comprising a plurality of engaging elements with sidewalls forming gaps, interposed by stabilizing elements, and in a substantially concentric arrangement with the stabilizing elements,
wherein said plurality of engaging elements is resilient and expandable in a radially outward direction from a compressed state towards an expanded state, in which expanded state the shortest distance between a point of said plurality of engaging elements and a central axis of said needle tip shielding device is longer than a shortest distance between said central axis and another point of said needle tip shielding device.

10. The needle tip shielding device according to claim 9, wherein the stabilizing elements include a first stabilizing element for stabilizing said needle tip shielding device in a catheter hub, and a second stabilizing element for slidingly engaging with a shaft of said needle, for stabilizing movement of said needle in a direction along the central axis of said needle tip shielding device and relative said needle tip shielding device.

11. The needle tip shielding device according to claim 10, wherein said second stabilizing element is provided with a hole extending in an axial direction of said fixing arrangement, through which hole said needle is configured to slide in a direction along the central axis of said needle tip shielding device and relative said needle tip shielding device.

12. The needle tip shielding device as claimed in claim 10, further comprising a resilient arm extending from the distal side of said fixing arrangement, wherein said resilient arm has a resting state, from which said resilient arm is configured to be forced to yield free passage in an axial direction of said fixing arrangement, said resilient arm being adapted for protecting or clamping said needle tip and wherein any straight imaginary line extending longitudinally in an axial direction of said fixing arrangement through a passage between said proximal side and said distal side, coincides with said resilient arm, when said resilient arm is in said resting state.

13. The needle tip shielding device according to claim 9, wherein said fixing arrangement is shaped as a circular or distorted cut cone or cylinder.

14. The needle tip shielding device according to claim 9, wherein said needle tip shielding device is a monolithic or homogenous injection molded needle tip shielding device made of a molded plastic material.

15. The needle tip shielding device according to claim 9, wherein the needle tip shielding device is made by molding a plastic or polymeric material.

16. A needle tip shielding device for protection of a needle tip of a needle, the device comprising:
a fixing structure including a proximal side, a distal side, and a plurality of engaging elements with sidewalls forming gaps, interposed by stabilizing elements, and in a substantially concentric arrangement with the stabilizing elements,
wherein said plurality of engaging elements is flexible and expandable in a radially outward direction from a compressed state towards an expanded state, in the expanded state a shortest distance between a point of said plurality of engaging elements and a central axis of the needle tip shielding device is longer than the shortest distance between said central axis and any other point of the needle tip shielding device.

17. The device according to claim 16, further comprising:
at least one first stabilizing element for stabilizing the needle tip shielding device in a catheter hub.

18. The device according to claim 16, further comprising:
at least one second stabilizing element for slidingly engaging with a shaft of said needle, for stabilizing movement of said needle in a direction along the central axis of said needle tip shielding device and relative said needle tip shielding device.

19. The device according to claim 16, wherein said fixing structure is shaped as a circular or distorted cut cone or cylinder.

20. The device according to claim 16, wherein the needle tip shielding device is a monolithic or homogenous injection molded needle tip shielding device made of a molded plastic material.

* * * * *